United States Patent
Werheit

(10) Patent No.: US 10,816,534 B2
(45) Date of Patent: Oct. 27, 2020

(54) YARN SENSOR FOR OPTICALLY SENSING A YARN MOVED IN THE LONGITUDINAL DIRECTION OF THE YARN

(71) Applicant: Saurer Spinning Solutions GmbH & Co. KG, Uebach-Palenberg (DE)

(72) Inventor: Patrick Werheit, Aachen (DE)

(73) Assignee: Saurer Spinning Solutions GmbH & Co. KG, Uebach-Palenberg (DE)

( * ) Notice: Subject to any disclaimer, the term of this patent is extended or adjusted under 35 U.S.C. 154(b) by 0 days.

(21) Appl. No.: 16/410,228

(22) Filed: May 13, 2019

(65) Prior Publication Data
US 2019/0353600 A1  Nov. 21, 2019

(30) Foreign Application Priority Data
May 15, 2018 (DE) .................. 10 2018 111 648

(51) Int. Cl.
*G01N 21/89* (2006.01)
*D01H 13/26* (2006.01)
(Continued)

(52) U.S. Cl.
CPC .......... *G01N 33/365* (2013.01); *D01H 13/165* (2013.01); *D01H 13/26* (2013.01);
(Continued)

(58) Field of Classification Search
CPC ...... D01H 13/165; D01H 13/26; D01H 13/32; D06H 3/08; G01B 11/08; G01B 11/10;
(Continued)

(56) References Cited

U.S. PATENT DOCUMENTS 4,213,056 A * 7/1980 Matsumura .......... G01N 33/365
250/559.01
4,490,618 A 12/1984 Cielo
(Continued)

FOREIGN PATENT DOCUMENTS

DE  41 22 305 A1  1/1993
EP  1 655 599 B1  9/2012
(Continued)

OTHER PUBLICATIONS

Search Report for corresponding European Patent Application No. 19172499.6, dated Nov. 7, 2019, all enclosed pages cited.

*Primary Examiner* — Gordon J Stock, Jr.
(74) *Attorney, Agent, or Firm* — Nelson Mullins Riley & Scarborough LLP

(57) ABSTRACT

In order to optically sense a yarn moved in the longitudinal direction of the yarn, a yarn sensor has a light source, a detector and a light guiding element. The yarn sensor is based on the effect of frustrated total internal reflection (FTIR). Because of the FTIR effect, scattered light exiting the light guiding element in the contact region between the yarn and an outer surface of the light guiding element is detected by means of the detector, in which case sensing of the yarn lying against the outer surface is enabled. Alternatively, the reduced intensity in the totally internally reflected beam is then sensed by the detector. The intensity in the totally internally reflected beam is reduced mainly by the scattered light coupled out of the light guiding element.

17 Claims, 3 Drawing Sheets

(51) Int. Cl.
*D01H 13/32* (2006.01)
*G01N 33/36* (2006.01)
*D01H 13/16* (2006.01)
*G01B 11/10* (2006.01)
*D06H 3/08* (2006.01)
*G01N 21/552* (2014.01)

(52) U.S. Cl.
CPC ............... *D01H 13/32* (2013.01); *D06H 3/08* (2013.01); *G01B 11/105* (2013.01); *G01N 21/8901* (2013.01); *G01N 21/8915* (2013.01); *G01N 21/552* (2013.01)

(58) Field of Classification Search
CPC ..... G01B 11/105; G01B 11/30; G01B 11/303; G01N 2021/458; G01N 2201/062; G01N 2201/0806; G01N 2201/08; G01N 33/36; G01N 33/365; G01N 33/367; G01N 21/552; G01N 21/8901; G01N 21/915; G01N 21/88; G01N 21/8803; G01N 21/8806; G01N 21/89; G01N 21/8903; G01N 21/8914; G01N 21/892; G01N 21/898; G01N 21/8983; G01N 21/952; G01N 21/95
See application file for complete search history.

(56) References Cited

U.S. PATENT DOCUMENTS

| | | | | |
|---|---|---|---|---|
| 4,970,402 | A * | 11/1990 | de Vuyst | B65H 63/065 250/559.12 |
| 5,194,911 | A * | 3/1993 | Stutz | D01G 23/06 19/0.23 |
| 5,371,584 | A * | 12/1994 | Scheinhutte | B65H 63/065 356/238.3 |
| 5,421,529 | A * | 6/1995 | Hans | B65H 63/0322 242/470 |
| 6,088,094 | A * | 7/2000 | Chu | B65H 63/065 19/65 A |
| 6,095,200 | A * | 8/2000 | Hellstroem | D03D 47/367 139/452 |
| 7,773,225 | B2 * | 8/2010 | Barea | B65H 63/0324 356/429 |
| 10,054,435 | B2 * | 8/2018 | Otsuka | G01N 21/4738 |
| 2002/0000526 | A1 * | 1/2002 | Delawski | D02J 1/08 250/559.4 |

FOREIGN PATENT DOCUMENTS

| | | | |
|---|---|---|---|
| WO | 93/12028 A1 | 6/1993 | |
| WO | WO-2004094285 A1 * | 11/2004 | ........... D03D 47/367 |
| WO | 2016/027792 A1 | 2/2016 | |

\* cited by examiner

YARN SENSOR FOR OPTICALLY SENSING A YARN MOVED IN THE LONGITUDINAL DIRECTION OF THE YARN

CROSS-REFERENCE TO RELATED APPLICATIONS

This application claims priority from German National Patent Application No. 10 2018 111 648.9, filed May 15, 2018, entitled "Garnsensor zum optischen Erfassen eines in seiner Längsrichtung bewegten Gams", the entire contents of which are incorporated herein by reference.

FIELD OF THE INVENTION

The subject matter of the invention relates to a yarn sensor for optically sensing a yarn moved in the longitudinal direction of the yarn. The invention also relates to a textile machine having the yarn sensor and a method for operating a yarn sensor.

BACKGROUND OF THE INVENTION

Yarn sensors are used at textile machines, such as spinning machines and winding machines. They are intended to monitor the yarn and/or the yarn quality. Such yarn sensors have a light source and a detector, in which case an optically operating monitoring system is provided in order to ensure corresponding signal capture. The contactless monitoring and scanning of the yarn occurs separately for each workstation. The use of a yarn monitoring system is particularly important for the textile machine and therefore also for the quality of the yarn.

The yarn monitoring system provides information about the presence of the yarn. In this case, the yarn sensor forms what is referred to as a thread monitor. Yarn sensors by means of which the yarn thickness or yarn quality is monitored have also been disclosed.

Thus, by optically sensing the yarn, the presence of the yarn can be monitored or the quality of the yarn can be determined. In order to determine the quality of the yarn, in particular the diameter of the yarn is determined and contaminants, more particularly foreign fibers, are detected.

In the case of the known optical yarn sensors, the yarn is guided within a measurement gap without contact. By means of the yarn and the air dragged in with the yarn, dust, dirt particles and finishing agents are conducted to the yarn sensor. These particles are deposited on the sensor surfaces of the yarn sensor, and this can cause a degree of soiling that leads to considerable distortions of measured values.

The soiling problem of yarn sensors has already been recognized. European Patent EP 1 655 599 B1 discloses a yarn sensor for optically scanning a yarn moved in the longitudinal direction of the yarn in a measurement gap, in the case of which essentially only light from a light source that is reflected by the yarn reaches two receivers for reflected light. Foreign influences, e.g. resulting from fibers or dust, can thereby be reduced.

International Patent Publication WO 93/12028 A1 discloses, for example, that the sensor surfaces of the yarn sensor are cleaned. In order to achieve cleaning of the sensor surfaces, the yarn is moved toward the sensor surface down to a small fixed distance. Because the yarn has a certain hairiness, a "brush effect" is achieved with respect to the optical inner surface. Around the running yarn, an air draft is produced by a boundary layer flow, and this air draft can also have a cleaning effect.

SUMMARY OF THE INVENTION

Proceeding therefrom, the objective of the present invention is that of increasing the reliability of the yarn sensor.

This aim is achieved according to the invention by means of a yarn sensor for optically sensing a yarn moved in the longitudinal direction of the yarn, the yarn sensor comprising: a light source, a detector, and a light guiding element for guiding light emitted by the light source, wherein a yarn guiding element is present to bring the yarn into contact with an outer surface of the light guiding element, and wherein at least part of the light is coupled out of the light guiding element by contact with the yarn, and the detector senses light influenced by the yarn.

There are advantageous developments and embodiments of the yarn sensor according to the invention.

In an embodiment of the invention, the yarn sensor is characterized in that the detector senses light coupled out of the light guiding element by the yarn.

In an embodiment of the invention, the yarn sensor is characterized in that the detector senses remaining light that is guided by the light guiding element and is not coupled out by the yarn.

In an embodiment of the invention, the yarn sensor is characterized in that the light guiding element is comprised at least partly of a transparent ceramic.

In an embodiment of the invention, the yarn sensor is characterized in that an outer surface of the light guiding element is convexly curved.

In an embodiment of the invention, the yarn sensor is characterized in that the detector is a spatially resolving detector.

In an embodiment of the invention, the yarn sensor is characterized in that the detector is an active pixel sensor.

In an embodiment of the invention, the yarn sensor is characterized in that the light guiding element is part of a yarn guiding element.

The features individually can be combined with one another in any desired, technically reasonable way and define further embodiments of the invention. Moreover, the features are defined in more detail and explained in the description, wherein additional preferred embodiment examples of the invention are presented.

According to the invention, a yarn sensor for optically sensing a yarn moved in the longitudinal direction of the yarn is proposed, comprising a light source, a detector and a light guiding element for guiding the light emitted by the light source. Yarn guiding elements are present in order to bring a yarn in contact with the outer surface of the light guiding element. The light guiding elements are designed in such a way that, by means of contact with the yarn, at least part of the light is coupled out of the light guiding element. The detector is arranged and designed in such a way that the detector senses light influenced by the yarn.

The yarn sensor according to the invention is based on the effect of frustrated total internal reflection (FTIR). Total internal reflection occurs at an interface between two light-absorbing media having different light propagation velocities when the angle of incidence exceeds a certain value, which is referred to as the critical angle of total internal reflection. The optical density of the air is substantially lower than the optical density of the yarn. The contact of the yarn at a contact area between the yarn and the outer surface of the light guiding element results in frustrated total internal reflection, because the index of refraction of the yarn is greater than the index of refraction of the air.

Because of the effect of frustrated total internal reflection, the light that exits the light guiding element in the contact region between the yarn and the outer surface of the light guiding element is scattered at the yarn. The scattered light propagates out of the light guiding element. Said scattered light can be detected directly or indirectly by means of the detector, in which case sensing of the yarn lying against the outer surface is enabled. Or in other words, the influence of the yarn on the light emitted by the light source is sensed. In principle, there are two options for this purpose, which can be used alternatively or in conjunction with each other.

According to a first embodiment, the detector is arranged and designed in such a way that the detector senses light that is coupled out of the light guiding element by the yarn.

According to a second embodiment, the detector is arranged and designed in such a way that the detector senses the remaining light that is guided by the light guiding element and is not coupled out by the yarn.

In the first embodiment of the yarn sensor according to the invention, the scattered light that is coupled out of the light guiding element is detected by the detector. This is the light that is reflected at the contact area between the yarn and the outer surface of the light guiding element. Alternatively or additionally, there is the possibility that the light guiding element is suitable and intended for guiding light reflected at the outer surface of the light guiding element to the detector. The reduced intensity in the totally internally reflected beam is then evaluated by means of the detector. The intensity in the totally internally reflected beam is reduced mainly by the scattered light coupled out of the light guiding element.

By means of the design of the optical yarn sensor according to the invention, the previous development of optically operating yarn sensors is left and a completely new path is taken. By using the FTIR effect, a yarn sensor is provided which has a simple design and is not sensitive to environmental influences. Because the moved yarn lies against the light guiding element during operation, the problems of soiling influences known in connection with known optical yarn sensors are largely avoided, because the yarn has a self-cleaning effect in the region of the contact area with the light guiding element.

The region of the light guiding element adjacent to the contact area is also cleaned. Because of the hairiness of the yarn, soiling is removed not only from the contact area between the yarn and the outer surface of the light guiding element but also from the region adjacent to the contact area. This cleaning effect is reinforced by a "chimney effect", because the moved yarn and the formed boundary layer flow produce an air draft.

The design of the yarn sensor according to the invention also enables a very compact construction, because the structure of the optical system can be minimized to only a very small number of components.

The yarn sensor according to the invention can be used as what is referred to as a thread monitor. The thread monitor provides information about whether a yarn is present or not.

The intensity of the scattered light coupled out of the light guiding element is proportional to the contact area of the yarn with the outer surface of the light guiding element. If the thread tension is constant, the diameter of the yarn can be inferred, and thus the yarn sensor can also provide information about the quality of the yarn. For example, knots in the yarn can be sensed.

Assuming that, for example, foreign fibers, dust, etc. have a different index of refraction from the yarn body, foreign fibers can be detected by means of the yarn sensor according to the invention.

Any arrangement is possible as the yarn guiding element. It only matters that the yarn is brought into contact with the light guiding element. For this purpose, the yarn guiding element can, for example, contain one guiding eye before and one guiding eye after the light guiding element in the thread running direction.

Because the yarn is guided in contact with the light guiding element, it is advantageous if the light guiding element at least partly consists of a transparent ceramic. The use of a ceramic has the advantage that the wear of the light guiding element can be kept low. The transparent ceramic can be an outer layer of a light guiding element. For example, the transparent ceramic can be connected to a glass body or plastic body, the connection being accomplished, for example, by means of a transparent adhesive. If a transparent ceramic is adhesively bonded to a plastic body, for example, it must be ensured that there are no air inclusions in the adhesive-bonding layer.

The outer surface of the light guiding element preferably has a convex curvature. Reliable contact of the yarn with the outer surface of the light guiding element is thus achieved.

According to another advantageous embodiment, the light guiding element has a circular cross-section. In particular, the light guiding element can be in the form of a round bar.

The light source is preferably suitable and intended for emitting an infrared light. In particular, the light source can comprise at least one light-emitting diode.

The detector is, in particular, a spatially resolving detector. Said detector has, for example, a CCD or CMOS array, a CCD or CMOS line. In particular, it is proposed that the detector is an active pixel sensor. The active pixel sensor has an integrated circuit with a series of pixel sensors. Each pixel sensor can comprise, for example, a photodiode with an active amplifier.

According to another advantageous embodiment of the yarn sensor according to the invention, it is proposed that the light guiding element is a part of a yarn guiding element. A yarn sensor formed in such a way has the advantage that the number of components can be reduced. Furthermore, because of the compact design of the yarn sensor, in particular also because the light guiding element is a part of a yarn guiding element, higher monitoring quality can be achieved in the spinning process.

The invention further relates to a textile machine having a yarn sensor according to the invention.

Furthermore, a method for operating a yarn sensor according to the invention is proposed. The invention therefore likewise relates to a method for optically sensing a yarn moved in the longitudinal direction of the yarn, by means of a light guiding element. According to the method according to the invention, light is guided by the light guiding element. The yarn is brought into contact with the outer surface of the light guiding element so that at least part of the light is coupled out of the light guiding element. Finally, the light influenced by the yarn is sensed. For this purpose, the light coupled out of the light guiding element by the yarn can be sensed. It is also possible to sense the remaining light that is guided by the light guiding element and is not coupled out by the yarn.

The light influenced by the yarn, having been sensed in such a way, can be evaluated. In this way, diameter deviations and contaminants can be sensed. It is also possible to evaluate merely the presence of the yarn or the thread.

BRIEF DESCRIPTION OF THE DRAWINGS

Further advantages and details of the yarn sensor according to the invention are explained on the basis of two preferred embodiment examples, without the subject matter of the invention being limited to these specific embodiment examples.

The figures show.

DESCRIPTION OF THE PREFERRED EMBODIMENTS

Figure 1:
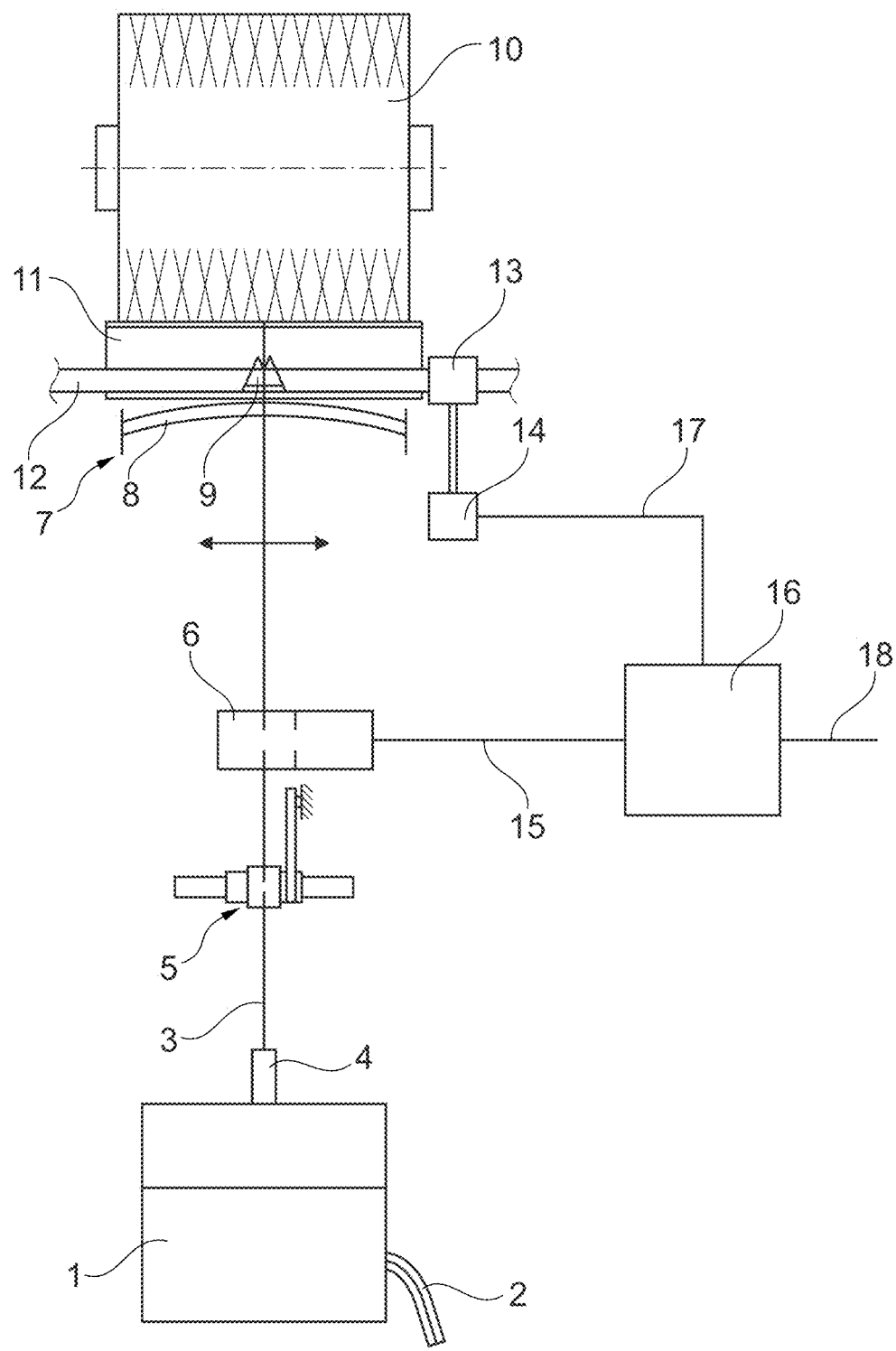
FIG. 1 is a schematic illustration of a workstation.

FIG. 1 shows a schematic illustration of a workstation of a textile machine according to the invention. In the embodiment example, the textile machine is designed as an open-end spinning machine. A fiber band 2 is fed to a spinning box 1. The yarn 3 produced in the spinning box 2 is pulled out via a draw-off tube 4 by means of a draw-off roller pair 5. The yarn 3 runs through a yarn sensor 6 according to the invention and is wound, across a bow 8, by a back-and-forth movement of a thread guide 9 of a traversing device 7 over a specified width to form a cross-wound package 10.

A friction roller 11 drives the cross-wound package 10. The thread guide 9 is arranged on a thread guide rod 12. The thread guide rod 12 is moved back and forth by a thread guide transmission 13. A drive unit 14 is provided in order to produce the back-and-forth movement of the thread guide transmission 13.

From the illustration of FIG. 1, it is clear that, in order to monitor the running yarn 3, the yarn sensor 6 is arranged above the draw-off roller pair 5 in the traversing region of the yarn 3. This is not mandatory. It is also possible for the yarn sensor 6 to be arranged before the draw-off roller pair 5. The arrangement of the yarn sensor 6 is shown as an example here. The yarn sensor 6 can be provided at suitable points of the yarn run.

The yarn sensor 6 is connected to a control device 16 by means of a signal line 15. The control device 16 is connected to the drive unit 14 by means of a further signal line 17. The drive unit 14 is preferably an electric motor. The control device 16 can be connected to further spinning positions, data processing devices and spinning machines (not shown) by means of a signal line 18.

Figure 2:
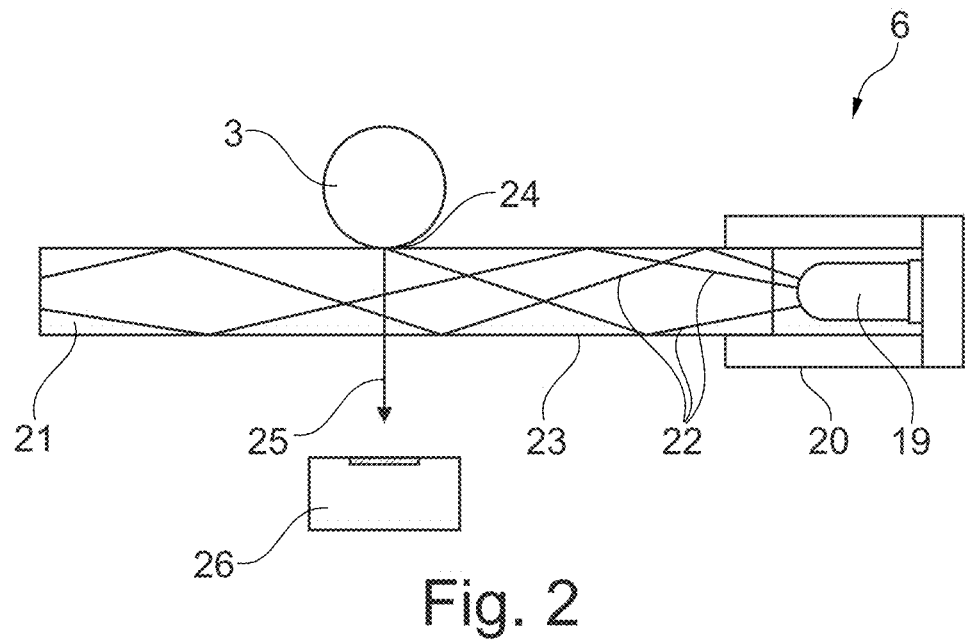
FIG. 2 is a schematic illustration of a first embodiment example of a yarn sensor.

In FIG. 2, a first embodiment example of a yarn sensor 6 is shown. The yarn sensor 6 has a light source 19. The light source 19 is preferably an infrared LED. The light source 19 is arranged in a housing 20. In the embodiment example shown, the housing 20 also serves as a retainer for a light guiding element 21. The light guiding element 21 is designed as a round bar. The material of the light guiding element 21 is preferably a transparent ceramic.

Only to illustrate the principle of the invention, reference number 22 is used to indicate beams that the light source 19 emits. The beams 22 are reflected at the outer surface 23. The light source 19 and the light guiding element 21 are designed in such a way that total internal reflection is achieved when no yarn is in contact with the outer surface 23 of the light guiding element 21.

In the embodiment example shown in FIG. 2, a yarn 3 is shown schematically. The yarn 3 lies against the outer surface 23 of the light guiding element 21. A contact area 24 lies between the yarn 3 and the outer surface 23. The contact of the yarn 3 with the light guiding element 21 results in frustrated total internal reflection in the region of the contact area 24, because the index of refraction of the yarn 3 is greater than the index of refraction of the air surrounding the yarn sensor 6. Because of the frustrated total internal reflection, the light that exits the light guiding element 21 in the region of the contact area 24 is scattered at the yarn. The scattered light propagates through the light guiding element 21, as indicated by the beam 25. Said scattered light is detected by means of a detector 26. The detector 26 provides signals, which can be fed to the control device 16, for example.

Figure 3:
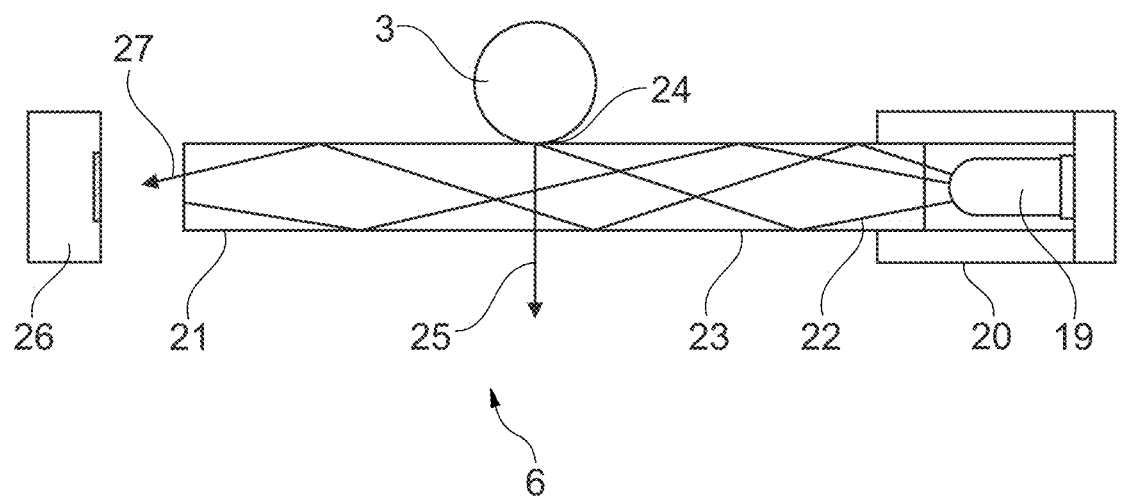
FIG. 3 is a schematic illustration of a second embodiment example of a yarn sensor.

FIG. 3 shows a second embodiment example of a yarn sensor. The yarn sensor 6 comprises a light source 19, which is arranged in a housing 20. The housing 20 also serves as a retainer for a light guiding element 21. Likewise in this embodiment example, the yarn 3 lies against an outer surface 23 of the light guiding element 21. The difference between the embodiment according to FIG. 3 and the embodiment according to FIG. 2 lies in the arrangement of the detector 26 and in the evaluation methodology associated therewith. Instead of the scattered light, which should be indicated by the beam 25 and which is coupled out of the light guiding element 21, the reduced intensity in the totally internally reflected beam 27 is evaluated.

Figure 4:
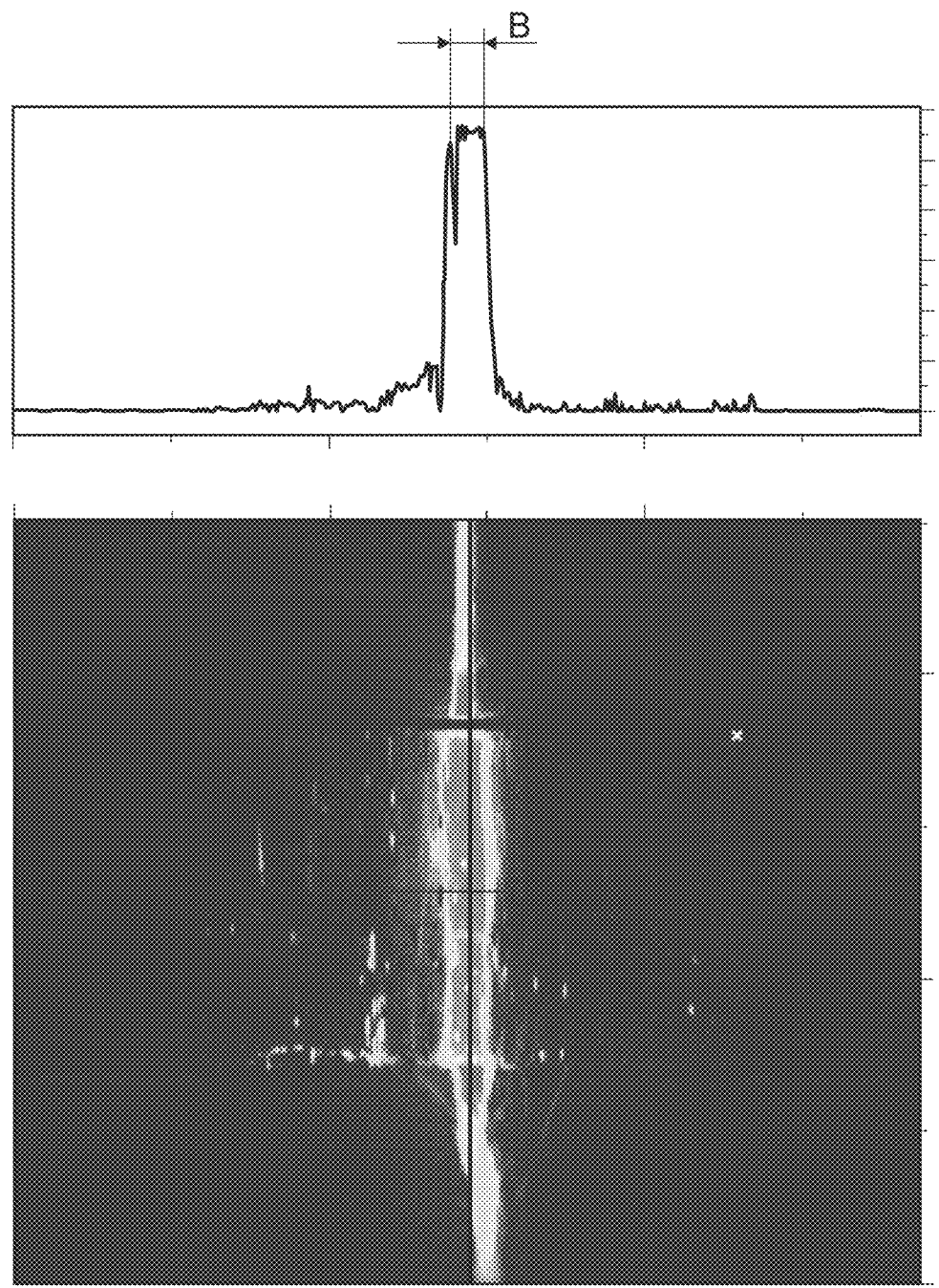
FIG. 4 is a snapshot of the yarn and a graph of an evaluation of a signal of a yarn sensor, which graph corresponds to the snapshot.

The detector 26 is preferably a pixel sensor, more particularly an active pixel sensor. In FIG. 4, a snapshot of the scattered light that a detector has sensed is shown. The evaluation of said snapshot is shown in a graph. It is clear that a yarn lies against the light guiding element.

The yarn diameter can be inferred from the width B of the detector signal, because, at constant thread tension, the scattered light is proportional to the yarn diameter. Thus, thin and thick places in the yarn can also be detected.

From the change in the detector signal over time, it can also be stated whether the tension of the yarn has changed.

LIST OF REFERENCE NUMBERS

1 Spinning box
2 Fiber band
3 Yarn
4 Draw-off tube
5 Draw-off roller pair
6 Yarn sensor
7 Traversing device
8 Bow
9 Thread guide
10 Cross-wound package
11 Friction roller
12 Thread guide rod
13 Thread guide transmission
14 Drive unit
15 Signal line
16 Control device
17 Signal line
18 Signal line
19 Light source
20 Housing
21 Light guiding element
22 Beams
23 Outer surface
24 Contact area
25 Beam
26 Detector
27 Beam It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements.

What is claimed is:

1. A yarn sensor for optically sensing a yarn moved in the longitudinal direction of the yarn, the yarn sensor comprising:
    a light source,
    a detector, and
    a light guiding element for guiding light emitted by the light source,
    wherein a yarn guiding element is present to bring the yarn into contact with an outer surface of the light guiding element, and
    wherein at least part of the light is coupled out of the light guiding element by contact with the yarn, and the detector senses light influenced by the yarn.

2. The yarn sensor according to claim 1, characterized in that the detector senses light coupled out of the light guiding element by the yarn.

3. The yarn sensor according to claim 1, characterized in that the detector senses remaining light that is guided by the light guiding element and is not coupled out by the yarn.

4. The yarn sensor according claim 1, characterized in that the light guiding element is comprised at least partly of a transparent ceramic.

5. The yarn sensor according to claim 1, characterized in that an outer surface of the light guiding element is convexly curved.

6. The yarn sensor according to claim 1, characterized in that the detector is a spatially resolving detector.

7. The yarn sensor according to claim 1, characterized in that the detector is an active pixel sensor.

8. The yarn sensor according to claim 1, characterized in that the light guiding element is part of a yarn guiding element.

9. A textile machine comprising a yarn sensor for optically sensing a yarn moved in the longitudinal direction of the yarn, wherein the yarn sensor comprises:
    a light source,
    a detector, and
    a light guiding element for guiding light emitted by the light source,
    wherein a yarn guiding element is present in order to bring the yarn into contact with an outer surface of the light guiding element, and
    wherein at least part of the light is coupled out of the light guiding element by contact with the yarn and the detector senses light influenced by the yarn.

10. The textile machine according to claim 9, characterized in that the detector senses light coupled out of the light guiding element by the yarn.

11. The textile machine according to claim 9, characterized in that the detector senses remaining light that is guided by the light guiding element and is not coupled out by the yarn.

12. The textile machine according claim 9, characterized in that the light guiding element is comprised at least partly of a transparent ceramic.

13. The textile machine according to claim 9, characterized in that an outer surface of the light guiding element is convexly curved.

14. The textile machine according to claim 9, characterized in that the detector is a spatially resolving detector.

15. The textile machine according to claim 9, characterized in that the detector is an active pixel sensor.

16. The textile machine according to claim 9, characterized in that the light guiding element is part of a yarn guiding element.

17. A method for optically sensing a yarn moved in the longitudinal direction of the yarn, by means of a light guiding element, comprising:
    guiding light by means of the light guiding element,
    bringing the yarn into contact with an outer surface of the light guiding element so that at least part of the light is coupled out of the light guiding element, and
    sensing the light influenced by the yarn.

* * * * *